(12) United States Patent
Uhrig et al.

(10) Patent No.: US 8,367,913 B2
(45) Date of Patent: Feb. 5, 2013

(54) METHODS FOR INCREASING TRANSFORMATION FREQUENCY THROUGH THE FOLIAR APPLICATION OF COPPER AMINO ACID CHELATE

(75) Inventors: Tim Uhrig, Rowan, IA (US); Paul Enger, Johnston, IA (US); Marie Michael, Urbandale, IA (US); Ron Christensen, Marshalltown, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 129 days.

(21) Appl. No.: 12/846,320

(22) Filed: Jul. 29, 2010

(65) Prior Publication Data

US 2011/0041209 A1 Feb. 17, 2011

Related U.S. Application Data

(60) Provisional application No. 61/230,024, filed on Jul. 30, 2009.

(51) Int. Cl.
*A01H 5/00* (2006.01)
(52) U.S. Cl. ..................... 800/320.1; 435/412
(58) Field of Classification Search .................. 800/278, 800/320.1; 435/468, 410, 412
See application file for complete search history.

(56) References Cited

U.S. PATENT DOCUMENTS

| | | | |
|---|---|---|---|
| 5,898,001 A | 4/1999 | Kumar et al. | |
| 6,235,529 B1 | 5/2001 | Lemaux et al. | |
| 6,274,791 B1 * | 8/2001 | Dhir et al. | 800/294 |
| 6,541,257 B2 | 4/2003 | Lemaux et al. | |
| 7,057,089 B2 * | 6/2006 | Ranch et al. | 800/293 |
| 7,102,056 B1 | 9/2006 | Lemaux et al. | |
| 8,007,846 B2 * | 8/2011 | Thompson et al. | 426/74 |
| 2007/0163007 A1 | 7/2007 | Ishida | |

FOREIGN PATENT DOCUMENTS

| | | |
|---|---|---|
| WO | WO 89/12102 A1 | 12/1989 |
| WO | WO 98/48613 A1 | 11/1998 |

OTHER PUBLICATIONS

ALBION Metalosate Plant Nutrition News. What exactly are the Metalosate products? vol. 1, No. 2 (May 2000), pp. 1-4.*
ALBION Metalosate. Copper amino acid chelate liquid foliar (Feb. 2009), 2 pp.*
Cheng et al. Genetic transformation of wheat mediated by *Agrobacterium tumefaciens*. Plant Physiol. (1997) 115: 971-980.*
Cheng et al. Invited review: factors influencing *Agrobacterium*-mediated transformation of monocotyledonous species. In Vitro Cell. Dev. Biol.—Plant 40:31-45, 2004.*
Holden. The utilization of ALBION technology products in comparison to a grower standard fertility management program for the production of strawberries in California. ALBION Conference on Plant Nutrition 2008, pp. 1-10.*
Ishida et al. *Agrobacterium*-mediated transformation of maize. Nature Protocols vol. 2, No. 7, 2007, 1614-1621.*
Praire Grains. Crop Development. Issue 86 2007 retrieved on Apr. 24, 2012. Retrieved from the Internet at <http://www.smallgrains.orf/springwh/Summer07/dev/dev.html> 9 pp.*
Wallace et al. Foliar fertilization with Metalosates. Journal of Plant Nutrition, 6(6), 551-557 (1983).*
Dahleen, L.S., "Improved Plant Regeneration from Barley Callus Cultures by Increased Copper Levels," *Plant Cell, Tissue and Organ Culture*, 1995, pp. 267-269, vol. 43.

* cited by examiner

*Primary Examiner* — June Hwu
(74) *Attorney, Agent, or Firm* — Alston & Bird LLP

(57) ABSTRACT

Methods for transforming an explant are provided. The methods may include applying copper amino acid chelate to a plant and transforming an explant obtained therefrom. The transformed explant may have increased transformation frequency relative to a control.

16 Claims, No Drawings

METHODS FOR INCREASING TRANSFORMATION FREQUENCY THROUGH THE FOLIAR APPLICATION OF COPPER AMINO ACID CHELATE

CROSS-REFERENCE TO RELATED APPLICATIONS

This application claims the benefit of U.S. Provisional Application No. 61/230,024, filed Jul. 30, 2009, which is hereby incorporated herein in its entirety by reference.

BACKGROUND OF THE INVENTION

High efficiency transformation of plants is important in analyzing the usefulness of a variety of genes. Further high efficiency transformation of monocots and dicots is also important because large numbers of transgenic plants are needed to study the effect of a particular gene within a given period of time. The ability to directly transform agronomically important plant species at a usable frequency and across a wide range of genetic diversity is important for the development of commercial hybrid products with improved traits including, but not limited to, insect resistance, disease resistance, herbicide resistance, increased yield, increased tolerance to environmental stresses (such as drought, heat, etc.), enhanced seed quality (such as increased or modified starch, oil and/or protein content), and the like.

Genetic improvement of various crop species by genetic engineering has sometimes been hindered because techniques for in vitro culture, transformation, and regeneration of model cultivars are less effective with commercial cultivars. It would be of great benefit to improve the ability to genetically engineer monocots such as maize and sorghum and dicots such as soybean to increase nutritional value, increase resistance to pests, diseases and environmental stress, and to enhance alternative uses.

There is a need, therefore, for efficient methods for transformation and regeneration that can be used with corn as well as a wide variety of monocots and dicots.

BRIEF SUMMARY OF THE INVENTION

Methods for increasing the frequency and/or efficiency of plant transformation are provided. The methods use copper amino acid chelate to affect transformation frequency and/or efficiency in monocotyledonous or dicotyledonous plants. The method includes applying an effective amount of copper amino acid chelate to a plant. Explants from plants treated with the copper amino acid chelate are transformed and may exhibit increased transformation frequency and/or efficiency compared to explants from non-treated plants. Also provided herein are explants and plants transformed by these methods. Accordingly, use of the methods described herein may be used to increase transformation frequency, or to transform plants in a faster and less expensive manner than use of traditional methods alone. Other objects, features, advantages and aspects of the present invention will become apparent to those of skill from the following description.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

Indeed, the invention may be embodied in many different forms and should not be construed as limited to the embodiments set forth herein; rather, these embodiments are provided so that this disclosure will satisfy applicable legal requirements.

Many modifications and other embodiments of the invention set forth herein will come to mind to one skilled in the art to which these inventions pertain having the benefit of the teachings presented in the foregoing descriptions. Therefore, it is to be understood that the invention are not to be limited to the specific embodiments disclosed and that modifications and other embodiments are intended to be included within the scope of the appended claims. Although specific terms are employed herein, they are used in a generic and descriptive sense only and not for purposes of limitation. The articles "a" and "an" are used herein to refer to one or more than one (i.e., to at least one) of the grammatical object of the article. By way of example, "an element" means one or more than one element.

It has been found that applications of copper amino acid chelate to a plant can improve the transformation frequency of an explant derived therefrom. Accordingly, provided herein are methods of transforming the explant from the plant treated with an effective amount of copper amino acid chelate. The term "effective amount" as used herein refers to the amount of copper amino acid chelate applied to a plant such that the copper amino acid chelate increases transformation efficiency or frequency of an explant obtained from the treated plant as compared to the transformation efficiency or frequency of a control, for example, an explant obtained from a non-treated plant. It is to be understood that no distinction is made herein between the terms "treat" and "apply" or their derivative forms and they are used interchangeably herein.

Any suitable copper amino acid chelate may be used to treat the plants so long as the copper amino acid chelate increases the transformation efficiency or frequency of an explant obtained from the plant. Various copper amino acid chelates are known and commercially available. See, for example, copper amino acid chelates available from Voigt Global Distribution Inc, (Lawrence, Kans.); American International Chemical, Inc. (Framingham, Mass.), and Albion (Clearfield, Utah). In one example, the copper amino acid chelate is a copper amino acid chelate commercially available from Albion and sold under the trademark of Metalosate® Copper foliar, in liquid and powder forms.

The copper amino acid chelate may include the copper amino acid chelate described in U.S. patent application publication no. 20070172551, herein incorporated by reference in its entirety. For example, the copper amino acid chelate may include copper that is bound to at least two different types of amino acids. The amino acids that can be used in the copper amino acid chelate include all essential and non-essential amino acids and corresponding salts. The amino acids may be chemically modified into amino acid analogs. Accordingly, the amino acids can be generally selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, and valine. The amino acids may each chelate with the copper (e.g., fully chelated compounds), or one amino acid may chelate with the copper and the other amino acid complexed (non-chelated) with the copper (i.e., an amino acid having only one bond with the mineral). As used herein, a "chelate" must have at least two coordination bonds within a single molecule, such as an amino acid.

The copper amino acid chelate may also include copper that is additionally complexed with an organic acid (non-chelated). In other instances, the copper amino acid chelate may comprise copper that is chelated by a first amino acid and complexed with at least one organic acid. Any suitable amount of copper may be used in the copper amino acid chelate. The amount of copper of the copper amino acid chelate can be varied in relation to the amino acid chelates. As such, by way of example, and not limitation, the copper content of the copper amino acid chelate may range from about 5% to about 50% by weight. Any suitable amount or ratio of amino acids may be used in the copper amino acid chelate. For example, a molar ratio of the first amino acid and the second amino acid may be from about 1:0.2 to about 1:7, from about 1:0.5 to about 1:5, or from about 1:1. These molar ratios are suitable for the following amino acid combinations: (a) glycine and methionine; (b) glycine and aspartic acid; (c) lysine and methionine; (d) lysine and aspartic acid; (e) methionine and aspartic acid; and others. However, the molar ratio of the glycine to lysine can be from about 1:0.09 to about 1:15, from about 1:0.1 to about 1:10, or from about 1:1. In some instances the copper amino acid chelate has increased solubility that results in increased bioavailability. The copper amino acid chelate may be water soluble or soluble in another solution.

As described elsewhere herein, an effective amount of copper amino acid chelate may be applied to the plant. The effective amount of the copper amino acid chelate may vary depending upon the solubility of the copper amino acid chelate, the type of plant to be treated, the type of explant obtained therefrom, and the desired increase in transformation efficiency or frequency of the explant.

When the copper amino acid chelate is available for foliar application, e.g. as a foliar fertilizer, the copper amino acid chelate is generally applied to the plant at the recommended field rate stated on the label. In accordance with the methods described herein, the copper amino acid chelate may be applied to the plant at a field rate that is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times the recommended rate of the foliar for the particular plant. In some instances, the amount of copper amino acid chelate is applied at a rate of from about 4 ounces per acre to about 140 ounces per acre or greater. The copper amino acid chelate applied may be present and applied at any suitable rate or percentage so long as the amount applied to the plant achieves an increase in transformation frequency. Accordingly, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 or greater ounces of copper amino acid chelate per acre may applied to the plant. The amount of copper amino acid chelate may be applied as a percentage of copper amino acid chelate per acre. For example, about 0.15, 0.25, 0.5, 0.75, 1, 1.25, 1.5 1.75, 2, 2.25, 2.5, 2.75, 3.0, 3.25, 3.5, 3.75, 4, 5, 6, 7, 8, 9, 10, 11, 12, 13, 14, 15, 16% or greater copper amino acid chelate per acre may be applied to a plant.

In one aspect, when the copper amino acid chelate is Metalosate® Copper foliar, the copper amino acid chelate may be applied to the plant at a field rate that is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times the recommended rate of the Metalosate® Copper foliar for a particular plant. In general, when the copper amino acid chelate is Metalosate® Copper liquid or powder foliar, the copper amino acid chelate is present at about 4% or 16% copper amino acid chelate respectively per gallon and may be applied to the plant at a field rate of from about 1.75 ounces Metalosate® Copper foliar per acre to about 140 ounces Metalosate® Copper foliar per acre. Accordingly, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 or greater ounces Metalosate® Copper foliar per acre may applied to the plant.

Application may be affected by any means known in the art. In one example the mode of application is by spraying the copper amino acid chelate on the plant, for example, using conventional ground or aerial application equipment. Typically, the copper amino acid chelate is applied to the foliage or above ground portions of the plant, especially to the leaves of the plant; however, in some instances, the copper amino acid chelate may be applied to explants which may increase transformation efficiency or frequency. Exemplary explants are known to one skilled in the art and are also described elsewhere herein.

The copper amino acid chelate is usually diluted in water and sprayed on the plant using a fine spray for complete leaf coverage. The spray volumes necessary to apply the desired amount of copper amino acid chelate can be readily determined by one skilled in the art and the copper amino acid chelate should be sufficiently diluted so that the chelate does not burn the leaves when applied. Treatments or applications may include a single application of copper amino acid chelate or multiple applications, for example, 1, 2, 3, 4, or 5 or more applications. Each application may deliver an effective amount of copper amino acid chelate or the effective amount may be achieved through multiple applications.

Applications may occur during any growth stage of the plant. Typically, the application times are during vegetative and/or reproductive stages, for example, during vegetative growth stages, such as V-1 through V-18, VT and R1 stages. V1-Vn stages are designated numerically and characterized by the uppermost leaf with a visible leaf collar where V1 stage is characterized by one visible leaf collar, V2 characterized by 2 visible leaf collars, through continual numerical designation to the last expanded leaf VT stage is characterized by full tassel branch emergence. R1 is characterized by first visible silks protruding outside the husk. In some instances, applications of copper amino acid chelate may be applied when the plant is under stress, for example, when the plant is undergoing a change from a vegetative to a reproductive stage. One skilled in the art will be familiar with and able to identify the various developmental stages. See, for example, Ritchie, S. W., J. J. Hanway, and G. O. Benson. 1993. Using the Iowa State University Leaf Collar Staging Method. How a Corn Plant Develops (SP-48). Iowa State Univ. In one aspect, a plant is treated with the copper amino acid chelate during its V-4, V-8 or V-12 stages. The V-4 stage is characterized by 4 leaf collars, the V-8 stage by 8 leaf collars, the V-10 stage by 10 leaf collars, and the V-12 stage by 12 leaf collars. For example, copper amino acid chelate may be applied to a maize plant at about 28, 42, 49 or 56 days after seeding which corresponds to stages V-4, V-8, V-10 and V-12 respectively. Foliar amino acid chelate applied at V4, V-8 and V-12 vegetative growth stages improved transformation frequency of immature embryos from maize treated with Metalosate® Copper liquid foliar maize. See Example 5. Foliar application of maize with Metalosate® Copper at field rates of 3.4 and 13.6 times the recommended field rate yielded a percent transformation frequency that is almost 30% greater than the control. See Table 2. As demonstrated herein, one skilled in the art would be able to determine the appropriate application timing, effective amount, and rate of application of copper amino acid chelate to increase transformation efficiency and frequency using the methods described herein.

Any plant species may be treated with the copper amino acid chelate, including, but not limited to, monocots and dicots. Examples of plant species of interest include, but are not limited to, maize (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

It will be understood by one skilled in the art that the explant may comprise a plant cell, a tissue or an organ. Exemplary explants for use with the methods include but are not limited to embryos, callus such as Type I or II, cell suspensions, cotyledons, hypocotyls, epicotyls, meristems, seedlings, seeds, leaves, stems, shoots, scutella, nodes, leaf bases, or roots. See U.S. patent application publication no. 20080280361, U.S. Pat. Nos. 5,569,834; 5,416,011; 5,824,877; 7,064,248. Additional explants include a tassel such as an immature tassel, an ear such as an immature ear, an embryo such as an immature or mature embryo, or zygotic embryo. As used herein, the term "zygotic embryo" is an embryo found inside a botanic seed produced by sexual reproduction. When the explant is an embryo from a maize plant, the method may include pollinating ears from the treated maize plant, harvesting the ears so that the ears or embryos may be prepared for transformation. See, for example, Green and Phillips (Crop Sci. 15:417-421, 1976). Maize immature embryos can be isolated from pollinated plants, as another example, using the methods of Neuffer et al. ("Growing Maize for genetic purposes." In: Maize for Biological Research W. F. Sheridan, Ed., University Press, University of North Dakota, Grand Forks, N. Dak. 1982.). The explant may be prepared using any suitable technique and may include, for example, isolating the explant from the plant, excising plant cell, tissue, or organ from the explant, sterilizing the plant cell, tissue, organ, or explant or combinations thereof.

Suitably prepared explants may be transformed. Numerous methods for introducing polynucleotides into explants are known and can be used to insert a polynucleotide of interest into the plant cell of the explant, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., Science 227:1229-31 (1985)), electroporation, micro-injection, and biolistic bombardment.

The polynucleotide may be any suitable polynucleotide. Polynucleotides suitable for use in the methods described herein may be either endogenous or heterologous to the plant cell of the explant to be transformed. Polynucleotides encompass all forms of nucleic acid sequences including, but not limited to, single-stranded, double-stranded, triplexes, linear, circular, branched, hairpins, stem-loop structures, branched structures, and the like. In some instances, the polynucleotide of interest may encode a polypeptide of interest which is expressed in the cell. The polynucleotide of interest may confer a particular trait of interest to the plant, for example, such as, but not limited to agronomic traits, disease resistant traits, insect resistant traits, herbicide tolerance traits, tolerance to herbicide-resistant weeds, efficient nitrogen use, nutritional enhancements, firmness, acidity content, sugar content, texture, oil, starch, carbohydrate, or nutrient metabolism, increased oil production, increased protein production, unique oil and protein production, increased fermentable starch production, increased content of essential amino acids, increased content of fatty acids and the like. In some instances, the polynucleotide of interest may suppress the expression of a target molecule in the plant cell, for example, and the polynucleotide may be a miRNA, a siRNA, an antisense polynucleotide and the like.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology*, supra, pp. 89-119. In one aspect, the expression cassette includes the "monocot-optimized" PAT gene (moPAT) driven by the ubiquitin promoter. See, for example, U.S. Pat. No. 6,096,947.

One widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) Crit. Rev. Plant Sci. 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Exemplary control sequences include promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid may also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 5,262,306 and Simpson, et al., (1986) *Plant Mol. Biol.* 6:403-15, all incorporated by reference in their entirety.

Transformation protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) Biotechniques 4:320-334), electroporation (Riggs, et al., (1986) Proc. Natl. Acad. Sci. USA 83:5602-5606, *Agrobacterium*-mediated transformation (U.S. Pat. Nos. 5,563,055 and 5,981,840), direct gene transfer (Paszkowski, et al., (1984) EMBO J. 3:2717-2722), and ballistic particle acceleration (see, for example, U.S. Pat. Nos. 4,945,050; 5,879,918; 5,886,244; and 5,932,782; Tomes, et al., (1995) in Plant Cell, Tissue, and Organ Culture: Fundamental Methods, ed. Gamborg and Phillips (Springer-Verlag, Berlin); McCabe, et al., (1988) Biotechnology 6:923-926); and Lec1 transformation (WO 00/28058). Also see, Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) Bio/Technology 6:923-926 (soybean); Finer and McMullen (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783; and 5,324,646; Klein, et al., (1988) Plant Physiol. 91:440-444 (maize); Fromm, et al., (1990) Biotechnology 8:833-839 (maize); Hooykaas-Van Slogteren, et al., (1984) Nature (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford (1995) Annals of Botany 75:407-413 (rice); Osjoda, et al., (1996) Nature Biotechnology 14:745-750 (maize via *Agrobacterium tumefaciens*); all of which are herein incorporated by reference.

Once transformed, these cells can be used to regenerate transgenic plants. Examples of methods for regenerating plant tissue are disclosed in Shahin, (1985) *Theor. Appl. Genet.* 69:235-40; U.S. Pat. No. 4,658,082; Simpson, et al., supra; and Weissbach and Weissbach, In: Methods for Plant Molecular Biology, (Eds.), Academic Press, Inc. San Diego, Calif., (1988).

Provided herein are methods for increasing the frequency or efficiency of plant transformation. As described above and in the examples below, the methods include introducing the polynucleotide of interest into a plant cell of the explant from the plant treated with the copper amino acid chelate to produce a transformed explant or plant cell.

The frequency of transformed plant cells achieved using these methods may be evaluated using any suitable method or technique, for example, molecular analysis. Putative transgenic events may be analyzed to confirm their transgenic nature. The choice of specific analytical test performed on any transgenic is dependent on the transgene. In general, almost all events are tested for the presence of the polynucleotide of interest by PCR, or a transgene product (mRNA, or protein) can also be assayed. For example, in those events produced with the GUS gene, tissues are stained with GUS histochemical assay reagent. Additionally, T0 plants can also be painted with bialaphos herbicide (1% v/v Liberty) if these plants were transformed with bar or pat gene. The subsequent lack of herbicide-injury lesion indicates the presence and action of the BAR/PAT transgene product, which conditions for herbicide resistance. Southern blotting may be utilized to determine copy number, insertion pattern, rearrangement and integration vector backbone DNA into the genome. For example, when using a visible marker such as red fluorescent protein (RFP), transformation frequencies may be determined by counting the numbers of embryos with large multicellular RFP positive cells clusters using a RFP microscope, and representing these as a percentage of the original number of embryos bombarded. Thus, the application of copper amino acid chelate to plants may be readily evaluated for its ability to increase transformation frequencies over the control treatment. Thus, one skilled in the art can readily determine frequency, i.e. the number of the explants producing transgenic events divided by the total explants *Agrobacterium* infected or bombarded.

To regenerate a plant, the method further includes selecting transformed plant cells or tissue so that it may be regenerated into a plant using standard methods known to one skilled in the art. The method may include regenerating the transformed cells or tissue on a regeneration media to produce a transformed plant. "Regenerating" as used herein refers to regenerating transformed plant cells or tissues into a plant. Methods for plant regeneration are known in the art. See, for example, Kamo et al. (Bot. Gaz 146(3):327-334, 1985), West et al. (The Plant Cell 5:1361-1369, 1993), and Duncan et al.

(Planta 165:322-332, 1985). The plant may be further cultured to allow for the growth of roots or shoots or both. Accordingly, a transformed plant using the methods described herein is also provided. In one aspect, the transformed plant is stably transformed.

EXAMPLES

The present invention is further defined in the following Examples, in which parts and percentages are by weight and degrees are Celsius, unless otherwise stated. The disclosure of each reference set forth herein is incorporated herein by reference in its entirety.

Example 1

Creation of a Hand-Held Sprayer

Any available application mechanism can be used to apply Metalosate® Copper foliar (Albion Laboratories, Inc. Clearfield Utah, product #7299, Metalosate® Copper, Metalosate® Copper MSDS No. 7299, Metalosate® Copper MSDS, Metalosate® Copper) to target maize plants of interest. Any timing of application of Metalosate® Copper foliar (Albion Laboratories, Inc. Clearfield Utah, product #7299, Metalosate® Copper, Metalosate® Copper MSDS No. 7299, Metalosate® Copper MSDS, Metalosate® Copper) to target plants. Any number of target plants can be used. Any available target plants can be used with the compositions and methods provided herein. Any available genotype can be used with the compositions and methods provided herein.

Step 1: A Quopak® adjustable spray bottle (VWR product 16344-509) was obtained through VWR International, Inc, Westchester, Pa.

Step 2: The intake tube on the spray head was removed, and the intake tube filter removed.

Step 3: The intake tube was cut to 18 cm in length, and reattached.

Step 4: 10 ml of water was placed into a triple rinsed BDH® Reference Standard Buffer bottle (VWR product # BDH5046-500 ml, VWR International, Inc, Westchester, Pa.).

Step 4: The Quopak® adjustable spray head and intake tube was attached to the rinsed BDH® Reference Standard Buffer bottle.

Step 5: The trigger mechanism was squeezed until air in the adjustable head and intake tube was removed.

Step 6: Each complete pump action was noted to eventually dispense 100 ml of water. This was repeated three times. Each complete pump action of the spray head applied approximately 1.33 ml of water in a fine mist.

Example 2

Calculation and Application of Metalosate® Copper Liquid Foliar

The target rates of Metalosate® Copper liquid foliar for this study were 0.0, 1.13, 3.4, 6.8, and 13.6 times the recommended field rate of 8 ounces per acre. Where:

Control 0×=no application.

Control 1.13× field rate=9.04 ounces Metalosate® Copper liquid foliar per acre 3.4× field rate=27.19 ounces Metalosate® Copper liquid foliar per acre 6.8× field rate=54.38 ounces Metalosate® Copper liquid foliar per acre 13.6× field rate=108.77 ounces Metalosate® Copper liquid foliar per acre Determination and Calculation of Spray Area:

Three PH17AW maize plants were treated as a single treatment unit for the purpose of this study. Three PH17AW maize plants occupy approximately 6.49 sq feet or approximately $1.4898*10^{-4}$ acres.

Determination and Calculation of Greenhouse Rates of Metalosate® Copper Liquid Foliar Per Three Plant Area:

The target rate of Metalosate® Copper liquid foliar per 3 plant area was calculated by conversion of ounces Metalosate® Copper liquid foliar per acre to milliliters (ml) Metalosate® Copper liquid foliar per acre. This Metalosate® Copper liquid foliar treatment value was then multiplied by $1.4898*10^{-4}$ acre. Where:

Control 0× rate=no application

Control 1.13× rate=0.04 ml of Metalosate® Copper liquid foliar applied to three PH17AW maize plants occupying approximately 6.49 sq feet 3.4× rate=0.12 ml of Metalosate® Copper liquid foliar applied to three PH17AW maize plants occupying approximately 6.49 sq feet 6.8× rate=0.24 ml of Metalosate® Copper liquid foliar applied to three PH17AW maize plants occupying approximately 6.49 sq feet 13.6× rate=0.48 ml of Metalosate® Copper liquid foliar applied to three PH17AW maize plants occupying approximately 6.49 sq feet Timeline of Metalosate® Copper Liquid Foliar Application to PH17AW Maize:

Maize was seeded and grown in flats (32 separable pots/sheet, Hummert International. St Louis, Mo.) for two weeks, then transplanted to 1-gallon sized pots. General plant care, photoperiod and temperature were typical for greenhouse grown maize plants. Metalosate® Copper liquid foliar was applied as a foliar spray to PH17AW maize plants at 2, 4, and either 5 or 6 weeks after transplant from flats to pots, which directly correspond to plant ages of approximately 28, 42, and 49 or 56 days after seeding, respectively. Plant ages of approximately 28, 42, and 49 or 56 days after seeding correspond to approximate V-stages of V-4, V-8, V-10, and V-12 respectively.

Preparation of Metalosate® Copper Liquid Foliar for Application to PH17AW Maize Plants:

Step 1: For each treatment rate applied, 40 ml water was measured into one Falcon® brand 35-2070 50 ml polypropylene tube (Becton Dickinson and Co. Franklin Lakes, N.J.).

Step 2: For each treatment rate applied, the appropriate volume of Metalosate® Copper liquid foliar (0.04, 0.12, 0.24, or 0.48 ml) was measured and added to 40 ml water contained in a single 50 ml polypropylene tube.

Step 3: Each 50 ml polypropylene tube containing either 0.04, 0.12, 0.24, or 0.48 ml Metalosate® Copper liquid foliar spray solutions was thoroughly mixed ensuring dispersion.

Step 4: Each 50 ml polypropylene tubes with appropriate spray solutions were transport to the site of application.

Foliar Application of Metalosate® Copper Liquid Foliar Solution to PH17AW Maize:

Step 1: Two weeks after transplant to pots (approximately 28 days after seeding or approximately stage V-4), 3 PH17AW maize plants were placed in linear fashion, evenly spaced, as to occupy approximately 6.49 square feet. Plants and spacing denoted as a "3-plant set" below.

Step 2: A single prepared spray solution in the 50 ml polypropylene tube was poured into the empty, triple rinsed BDH® reference standard buffer bottle.

Step 3: The calibrated Quopak® adjustable spray head was attached to the BDH® reference standard buffer bottle containing appropriate Metalosate® Copper liquid foliar and water solution. The calibrated Quopak® adjustable spray head with BDH® reference standard buffer bottle is denoted as "spray unit" below.

Step 4: Half the appropriate Metalosate® Copper liquid foliar/water solution was applied to one side of the 3-plant set. Spray pattern to one side of the 3-plant set was side-to-side, top-to-bottom. Spray was even, runoff on leaves avoided, and complete coverage of 3-plant set ensured. Fifteen complete pump actions of the Quopak® adjustable spray head applied half the spray volume to one side of the 3-plant set.

Step 5: The same Metalosate® Copper liquid foliar solution was applied to the opposing side of 3-plant set following the application methods in step 4.

Step 6: The spray unit was thoroughly rinsed with water ensuring removal of solution residue.

Step 7: Steps 1-6 in this section were repeated for each Metalosate® Copper liquid foliar solution.

Step 8: Steps 1-7 were repeated at 42, and 49 or 56 days after seeding to each of the 3-plant sets.

Determining Changes in *Agrobacterium*-Meditated Transformation Frequency Rates Using Increased or Decreased Number of Applications of Metalosate® Copper Liquid Foliar to Target PH17AW Plants.

Transformation frequency may be improved by using fewer than three, pre-harvest applications of Metalosate® Copper to PH17AW target plants using the above steps as described herein in Example 2.

Transformation frequency may be improved by using three or more pre-harvest applications of Metalosate® Copper to PH17AW target plants using the above steps as described herein in Example 2.

Transformation frequency may be improved by applying more than 13.6 times the recommended field rate of 8 ounces per acre of Metalosate® Copper liquid foliar to PH17AW target plants using the above steps as described herein in Example 2.

Example 3

Pre-Pollinated PH17AW Maize Ear Preparation and Controlled Pollination

Step 1: Newly emerged ear shoots of treated and non-treated PH17AW maize plants were covered with a single Lawson parchment shoot bag (product #GB205, Seedburo Equipment Co. Des Plaines Ill.).

Step 2: Four to six days after first silk emergence of the covered PH17AW maize ear shoot, fresh pollen of the same genotype was collected, the parchment shoot bag removed from the PH17AW maize ear, fresh pollen placed on the ear shoot silks (denoted as "sib pollinated"), and the freshly pollinated silks and ear shoot covered with a Lawson Maize Tassel Bag (product #GB402, Seedburo Equipment Co. Des Plaines Ill.).

Step 3: Pollinated ears were left to develop under normal greenhouse conditions for nine to ten days until such time as the ears were ready for harvest and subsequent embryo excision.

Example 4

PH17AW Maize Harvest and Transformation

Maize transformation via *Agrobacterium tumefaciens* was practiced as detailed in Zhao and Ranch, *Transformation of Maize Via Agrobacterium tumefaciens Using a Binary Co-Integrate Vector System*, in Plant Cell Culture Protocols, V. Loyola-Vargas and F. Vazquez-Flota, Editors, Humana Press: Totowa N.J. p. 315-324 (2005), and Ranch et al (U.S. Pat. No. 7,022,894). Plants of PH17AW were treated with Metalosate® Copper liquid foliar as described in Examples 1-3. Ears from the plants were pollinated, harvested 7-10 days after pollination, and aseptically prepared following standard methods for maize transformation of immature embryos. The DNA vector was PHP17112 (*Agrobacterium tumefaciens* strain LBA4404). PHP17112 is comprised of RB-ubi:zm5utr:ubi1zmintron1:GUS:st-1s1intron2gusexon2:pinii term//camv35senh:camv35s:adh1 intron1:bar:pinii-LB, and it was constructed using the methods of Komari et al, The Plant Journal (1996) 10(1):165-174. BAR was the selectable marker gene, and transgenic events were selected under herbicide selection. After infection and co-culture at 21° C., transgenic events were selected under bialaphos selection. After about 6-8 weeks, transgenic events were picked from the various treatments and scored as described in Example 5.

Example 5

Calculation of Transformation Frequency and Statistical Analysis

Transformation data was collected on an individual ear basis and assembled into Table 1. Transformation frequency was calculated on a per treatment basis where:

% Embryo Transformation Frequency=total number of transformed embryos(events)per treatment/ total number of harvested embryos per treatment.

Table 1 contains data from the foliar application of Metalosate® Copper liquid foliar to PH17AW maize. Data is presented on a treatment basis.

TABLE 1

Pilot Data from Foliar Application of Copper Metalosate to Maize and resultant Embryo Transformation Frequency

| Genotype | Field rate | Ounces Copper Metalosate/A | Gallons Water/ Acre | Spray schedule (weeks after transplant to pots)* | Plant # | #embryos per ear | #events per ear | % Embryo Transformation Freq/ Treatment | Standard error of % Transformation Frequency |
|---|---|---|---|---|---|---|---|---|---|
| PH17AW | 0X | 0 | 0 | NA | 78255836 | 113 | 5 | | |
| PH17AW | 0X | 0 | 0 | NA | 78255834 | 90 | 9 | | |
| PH17AW | 0X | 0 | 0 | NA | 78255835 | 150 | 5 | | |
| Total Embryos | | | | | | 353 | 19 | 5.38% | 1.20% |
| PH17AW | 1.13x | 9.0642 | 70.82 | 2, 4, 6 | 78410595 | 107 | 24 | | |
| PH17AW | 1.13x | 9.0642 | 70.82 | 2, 4, 6 | 78410594 | 156 | 8 | | |
| PH17AW | 1.13x | 9.0642 | 70.82 | 2, 4, 6 | 78410593 | 120 | 12 | | |
| PH17AW | 1.13x | 9.0642 | 70.82 | 2, 4, 5 | 78577882 | 60 | 4 | | |
| PH17AW | 1.13x | 9.0642 | 70.82 | 2, 4, 5 | 78577881 | 110 | 9 | | |
| PH17AW | 1.13x | 9.0642 | 70.82 | 2, 4, 5 | 78577883 | 60 | 9 | | |
| PH17AW | 1.13x | 9.0642 | 70.82 | 2, 4, 6 | 78577893 | 110 | 3 | | |
| Total Embryos | | | | | | 723 | 69 | 9.54% | 1.09% |
| PH17AW | 3.4x | 27.19 | 70.82 | 2, 4, 6 | 78410596 | 115 | 31 | | |
| PH17AW | 3.4x | 27.19 | 70.82 | 2, 4, 6 | 78410597 | 100 | 51 | | |
| PH17AW | 3.4x | 27.19 | 70.82 | 2, 4, 6 | 78410598 | 127 | 19 | | |
| PH17AW | 3.4x | 27.19 | 70.82 | 2, 4, 5 | 78577885 | 120 | 66 | | |
| PH17AW | 3.4x | 27.19 | 70.82 | 2, 4, 5 | 78577886 | 154 | 34 | | |
| PH17AW | 3.4x | 27.19 | 70.82 | 2, 4, 5 | 78577884 | 18 | 3 | | |
| PH17AW | 3.4x | 27.19 | 70.82 | 2, 4, 6 | 78577898 | 72 | 8 | | |
| PH17AW | 3.4x | 27.19 | 70.82 | 2, 4, 6 | 78577897 | 97 | 26 | | |
| Total Embryos | | | | | | 803 | 238 | 29.64% | 1.61% |
| PH17AW | 6.8x | 54.38 | 70.82 | 2, 4, 6 | 78410599 | 140 | 33 | | |
| PH17AW | 6.8x | 54.38 | 70.82 | 2, 4, 6 | 78410601 | 120 | 20 | | |
| PH17AW | 6.8x | 54.38 | 70.82 | 2, 4, 5 | 78577889 | 80 | 13 | | |
| PH17AW | 6.8x | 54.38 | 70.82 | 2, 4, 5 | 78577887 | 127 | 9 | | |
| PH17AW | 6.8x | 54.38 | 70.82 | 2, 4, 6 | 78577899 | 8 | 7 | | |
| PH17AW | 6.8x | 54.38 | 70.82 | 2, 4, 5 | 78577888 | 55 | 27 | | |
| PH17AW | 6.8x | 54.38 | 70.82 | 2, 4, 6 | 78577901 | 80 | 7 | | |
| PH17AW | 6.8x | 54.38 | 70.82 | 2, 4, 6 | 78577900 | 90 | 20 | | |
| Total Embryos | | | | | | 700 | 136 | 19.43% | 1.50% |
| PH17AW | 13.6x | 108.77 | 70.82 | 2, 4, 6 | 78410603 | 140 | 7 | | |
| PH17AW | 13.6x | 108.77 | 70.82 | 2, 4, 6 | 78410604 | 130 | 45 | | |
| PH17AW | 13.6x | 108.77 | 70.82 | 2, 4, 6 | 78410602 | 110 | 26 | | |
| PH17AW | 13.6x | 108.77 | 70.82 | 2, 4, 5 | 78577891 | 50 | 28 | | |
| PH17AW | 13.6x | 108.77 | 70.82 | 2, 4, 5 | 78577890 | 44 | 24 | | |
| PH17AW | 13.6x | 108.77 | 70.82 | 2, 4, 5 | 78577892 | 95 | 33 | | |
| PH17AW | 13.6x | 108.77 | 70.82 | 2, 4, 6 | 78577904 | 116 | 27 | | |
| PH17AW | 13.6x | 108.77 | 70.82 | 2, 4, 6 | 78577903 | 110 | 39 | | |
| PH17AW | 13.6x | 108.77 | 70.82 | 2, 4, 6 | 78577902 | 130 | 30 | | |
| Total Embryos | | | | | | 925 | 259 | 28.00% | 1.48% |

*2, 4, 5, 6 weeks after transplant = plant ages of approximately 28, 42, and 49 or 56 days after seeding = approximate V-Stages of V-4, V-8, V-10, and V-12

Statistical Analysis:
Differences in the transformation frequency between treatments were analyzed using following binomial model (1):

$$y_{ij} = \mu_i + \epsilon_{ij}$$

$$\mu_i \sim iddB(n,p)_{Field\ Rate} \text{ and } \epsilon_{ij} \sim iddB(n,p)_{error}$$

Where $\mu_i$ denotes the mean of the $i^{th}$ field rate (fixed effect) and $\epsilon_{ij}$ denotes the effect of the plant assigned the $i^{th}$ entry (random effect or residual). Notation $\sim iid\ B(n, p)_{Field\ Rate}$ denotes a random variable that is identically independently distributed (iid) as binomial with 'n' occurrences out of 'p' chances. A table giving the numbers of transformed/total embryos for each variable was entered into PROC GLIMMIX of the SAS system was used to obtain Restricted/Residual Maximum Likelihood (REML) estimates of the variance components which were used to provide estimates of the effects of the field rate. For the table, PROC GLIMMIX estimated the transformation frequency in the observed scale by use of the ILINK option for each field rate as well as the difference between field rates; from this the p-value was generated. Significance was assessed at the 5% level. Results are presented in Table 2.

Table 2 shows the mean percent transformation frequency, mean transformation frequency on a treatment basis at various field rate treatments, standard error, and level of significance at the 0.05 level.

TABLE 2

| | % Embryo Transformation Frequency | | |
|---|---|---|---|
| Field Rate | Mean % Transformation | Standard error of % Transformation Frequency | 0.05 level of significance[1] |
| 0X | 5.38% | 1.20% | a |
| 1.13X | 9.54% | 1.09% | b |
| 3.4X | 29.64% | 1.61% | d |
| 6.8X | 19.43% | 1.50% | c |
| 13.6X | 28.00% | 1.48% | d |

[1]Treatment means in same column without a common superscript letter differ ($p \leq .05$). All added levels of Metalosate® Copper liquid foliar to PH17AW significantly increased the maize transformation frequency with the largest improvement observed at the 3.4X and 13.6X rates when compared to the 0X Field Rate.

Example 6

Calculation and Application of Metalosate® Copper Liquid Foliar Utilizing One Application Rate and Two Timelines Determination and Calculation of Greenhouse Rates of Metalosate® Copper Liquid Foliar to PH17AW Maize Plants Utilizing Two Application Timing Regiments:

The target rate of Metalosate® Copper liquid foliar per 3 plant area was calculated by conversion of ounces Metalosate® Copper liquid foliar per acre to milliliters (ml) Metalosate® Copper liquid foliar per acre as described in Example 2. This Metalosate® Copper liquid foliar treatment value was then multiplied by $1.4898*10^{-4}$ acre as stated above. Quantity of liquid application was calculated where 0.12 ml Metalosate® Copper liquid foliar was applied per 3 plants occupying 3 plant area as described in Example 2. Further calculations show where 3 plants occupy 6.49 sq. feet and receive 0.12 ml Metalosate® Copper liquid foliar, one individual plant occupies 2.16 sq feet and receives 0.04 ml Metalosate® Copper liquid foliar. Applications below are applied on a individual plant basis where each plant occupies 2.16 sq feet and receives 0.04 ml Metalosate® Copper liquid foliar. Application of Metalosate® Copper Liquid Foliar was Applied on an Individual per Plant Basis as Calculated above where:

Control 0x rate=no application 3.4x rate=Metalosate® Copper liquid foliar applied to six PH17AW maize plants where, individual PH17AW maize plants occupying 2.16 sq. feet each, received 0.04 ml Metalosate® Copper liquid foliar.

Two Timelines of Metalosate® Copper Liquid Foliar Application to PH17AW Maize:

Timeline One: Maize was seeded and grown in flats (32 separable pots/sheet, Hummert International. St Louis, Mo.) for two weeks, then transplanted to 1-gallon sized pots. General plant care, photoperiod and temperature were typical for greenhouse grown maize plants. Metalosate® Copper liquid foliar was applied as a foliar spray to PH17AW maize plants at 6 weeks after transplant from flats to pots, which directly correspond to plant ages of approximately 56 days after seeding, respectively. Plant ages of approximately 56 days after seeding correspond to approximate V-stage of V-12. Metalosate® Copper liquid foliar was applied as a foliar spray to PH17AW maize plants at 6 weeks after transplant from flats to pots, which directly correspond to plant ages of approximately 56 days after seeding, Timeline Two: Maize was seeded and grown in flats (32 separable pots/sheet, Hummert International. St Louis, Mo.) for two weeks, then transplanted to 1-gallon sized pots. General plant care, photoperiod and temperature were typical for greenhouse grown maize plants. Metalosate® Copper liquid foliar was applied as a foliar spray to PH17AW maize plants at 2, 4, and 6 weeks after transplant from flats to pots, which directly correspond to plant ages of approximately 28, 42, and 56 days after seeding, respectively. Plant ages of approximately 28, 42, and 56 days after seeding correspond approximate V-stages of V-4, V-8, and V-12 respectively.

Preparation of Metalosate® Copper Liquid Foliar for Application to PH17AW Maize Plants:

Step 1: For each treatment rate applied, 40 ml water was measured into one Falcon® brand 35-2070 50 ml polypropylene tube (Becton Dickinson and Co. Franklin Lakes, N.J.).

Step 2: For the treatment rate applied, the appropriate volume of Metalosate® Copper liquid foliar (0.12 ml) was measured and added to 40 ml water contained in a single 50 ml polypropylene tube.

Step 3: The 50 ml polypropylene tube containing 0.12 ml Metalosate® Copper liquid foliar spray solutions was thoroughly mixed ensuring dispersion.

Step 4: The 50 ml polypropylene tubes with appropriate spray solutions were transport to the site of application.

Foliar Application of Metalosate® Copper Liquid Foliar Solution to PH17AW Maize Utilizing Timeline One:

Step 1: Six weeks after transplant to pots (approximately 56 days after seeding or approximately stage V-12), 6 PH17AW maize plants were placed in linear fashion, evenly spaced, such that each plant occupied approximately 2.16 square feet. Plants and spacing denoted as a "6-plant set" below.

Step 2: The calibrated Quopak® adjustable spray head was placed into the Falcon® brand 35-2070 50 ml polypropylene tube (Becton Dickinson and Co. Franklin Lakes, N.J.) containing the 40 ml prepared solution of Metalosate® Copper liquid foliar and water. The calibrated Quopak® adjustable spray head with the Falcon® brand 35-2070 50 ml polypropylene tube (Becton Dickinson and Co. Franklin Lakes, N.J.) is denoted as "spray unit" below.

Step 3: One-sixth (5.65 ml) of the 40 ml prepared Metalosate® Copper liquid foliar/water solution was applied to one side of the $1^{st}$ plant in the 6-plant set. Spray pattern to one side of the individual plant set was top-to-bottom. Spray was even, runoff on leaves avoided, and complete coverage of individual plant ensured. Five complete pump actions of the Quopak® adjustable spray head applied 5.65 ml to one side of the individual plant.

Step 4: Step 3 was repeated for each plant of the 6-plant set.

Step 5: Another 40 ml of Metalosate® Copper liquid foliar solution was prepared and one-sixth (5.65 ml) applied to the opposing side of the $1^{st}$ plant of the 6-plant set following the application methods in step 3.

Step 6: Step 5 was repeated for each of the remaining plants of the 6-plant set. The spray unit was thoroughly rinsed with water ensuring removal of solution residue.

Foliar Application of Metalosate® Copper Liquid Foliar Solution to PH17AW Maize Utilizing Timeline Two:

Step 1: Two weeks after transplant to pots (approximately 28 days after seeding or approximately stage V-4), 6 PH17AW maize plants were placed in linear fashion, evenly spaced, as to each plant should occupy approximately 2.16 square feet. Plants and spacing denoted as a "6-plant set" below.

Step 2: The calibrated Quopak® adjustable spray head was placed into the Falcon® brand 35-2070 50 ml polypropylene tube (Becton Dickinson and Co. Franklin Lakes, N.J.) containing the 40 ml prepared solution of Metalosate® Copper liquid foliar and water. The calibrated Quopak® adjustable spray head with the Falcon® brand 35-2070 50 ml polypropylene tube (Becton Dickinson and Co. Franklin Lakes, N.J.) is denoted as "spray unit" below.

Step 3: One-sixth (5.65 ml) of the 40 ml prepared Metalosate® Copper liquid foliar/water solution was applied to one side of the $1^{st}$ plant in the 6-plant set. Spray pattern to one side of the individual plant set was top-to-bottom. Spray was even, runoff on leaves avoided, and complete coverage of individual plant ensured. Five complete pump actions of the Quopak® adjustable spray head applied 5.65 ml to one side of the individual plant.

Step 4: Step 3 was repeated for each plant of the 6-plant set.

Step 5: Another 40 ml of Metalosate® Copper liquid foliar solution was prepared and one-sixth (5.65 ml) applied to the opposing side of the $1^{st}$ plant of the 6-plant set following the application methods in step 3.

Step 6: Step 5 was repeated for each of the remaining plants of the 6-plant set. The spray unit was thoroughly rinsed with water ensuring removal of solution residue.

Step 7: Steps 1-6 were repeated at 42, and 56 days after seeding to each of the 6-plant sets.

Treated and non-treated PH17AW plants were pollinated as described in Example 3. Transformation was performed as described in Example 4, using constructs comprising a moPAT selectable marker. After infection and co-culture at 21° C., transgenic events were selected under bialaphos selection. After about 6-8 weeks, transgenic events were picked from the various treatments and scored as described in Example 5. The results from these treatment regimes are presented in Example 7.

Example 7

Calculation of Transformation Frequency and Statistical Analysis

Transformation data was collected on an individual ear basis and assembled into Table 3, 4, and 5 for Timeline Two, Timeline One, and both Timelines respectively. Transformation frequency was calculated on a per treatment basis where:

% Embryo Transformation Frequency=total number of transformed embryos(events)per treatment/ total number of harvested embryos per treatment.

Table 3 contains data from the 3.4x foliar application of Metalosate® Copper liquid foliar to PH17AW maize occurring at 6 weeks after transplant from flats to pots, which directly correspond to plant ages of approximately 56 days after seeding, respectively. Plant ages of approximately 56 days after seeding correspond approximate V-stage of V-12. Data is presented on a treatment basis.

TABLE 3

Transformation Frequency with Copper Sprayed PH17AW maize plants, Copper Spray 3.4x at 6 Weeks after transplant.

| Table 3 | | | | | **PHP | | | |
|---|---|---|---|---|---|---|---|---|
| Copper | Data | 33949 | 37932 | 38570 | 39037 | 39663 | 39669 | Total |
| Control | Sum of # Ears | 3 | 5 | 5 | 5 | 3 | 4 | 25 |
| | Sum of # callus events | 210 | 116 | 102 | 194 | 67 | 243 | 932 |
| | Sum of # Emb | 540 | 576 | 372 | 569 | 437 | 783 | 3277 |
| | Sum of % Transformation Frequency | 0.3888 | 0.2013 | 0.2741 | 0.3409 | 0.1533 | 0.3103 | 0.2844* |
| 3.4x Rate | Sum of # Ears | 3 | 6 | 4 | 4 | 3 | 5 | 25 |
| | Sum of # callus events | 128 | 188 | 156 | 204 | 63 | 212 | 951 |
| | Sum of # Emb | 538 | 702 | 474 | 591 | 415 | 1008 | 3728 |
| | Sum of % Transformation Frequency | 0.2379 | 0.2678 | 0.3291 | 0.3451 | 0.1518 | 0.2103 | 0.2550* |

Chi square = 7.62 Statistically significantly different at 1% ($p \leq .01$) level between the Control treatment and the 3.4x foliar application of Metalosate ® Copper liquid foliar.
*Mean % Transformation frequency of treatment
**PHP = construct identification number Table 3 Statistical Analysis:
Differences in the transformation frequency between treatments were analyzed using Chi Square. Mean transformation frequency was statistically significant (Chi square=7.62, $p \leq 0.01$) where application of 3.4× Metalosate® Copper liquid foliar to PH17AW maize occurring at 6 weeks after transplant yielded significantly reduced transformation frequency when compared to the control.

Table 4 contains data from the 3.4× foliar application of Metalosate® Copper liquid foliar to PH17AW maize plants at 2, 4, and 6 weeks after transplant from flats to pots, which directly correspond to plant ages of approximately 28, 42, and 56 days after seeding, respectively. Plant ages of approximately 28, 42, and 56 days after seeding correspond approximate V-stages of V-4, V-8, and V-12 respectively.

TABLE 4

Transformation Frequency with Copper Sprayed PH17AW maize plants, Copper Spray 3.4× at 2, 4, and 6 Weeks

| Table 4 | | **PHP | | | | | |
|---|---|---|---|---|---|---|---|
| Copper | Data | 37049 | 38064 | 38067 | 39633 | 39906 | Total |
| Control | Sum of # Ears | 2 | 2 | 4 | 2 | 6 | 16 |
| | Sum of # callus events | 9 | 106 | 65 | 118 | 84 | 382 |
| | Sum of # Emb | 245 | 305 | 425 | 305 | 1082 | 2362 |
| | Sum of % Transformation Frequency | 0.03673 | 0.34754 | 0.15294 | 0.38688 | 0.07763 | 0.16172* |
| 3.4× rate | Sum of # Ears | 2 | 2 | 3 | 2 | 4 | 13 |
| | Sum of # callus events | 9 | 148 | 51 | 50 | 136 | 394 |
| | Sum of # Emb | 225 | 317 | 335 | 243 | 626 | 1746 |
| | Sum of % Transformation Frequency | 0.04 | 0.46687 | 0.15223 | 0.20576 | 0.21725 | 0.22565* |

Chi square = 26.78, Statistically significantly different at 0.1% ($p \leq .001$) level between the Control treatment and the 3.4× foliar application of Metalosate ® Copper liquid foliar.
*Mean % Transformation frequency of treatment
**PHP = construct identification number Table 4 Statistical Analysis:
Differences in the transformation frequency between treatments were analyzed using Chi Square. Mean transformation frequency was statistically significant (Chi square=26.78, $p \leq 0.001$) where, application of 3.4× Metalosate® Copper liquid foliar to PH17AW maize occurring at 2, 4, 6 weeks after transplant yielded significantly increased transformation frequency when compared to the control (no application.

Table 5 contains presents consolidated averaged data from Table 3 and 4. from the 3.4× foliar application of Metalosate® Copper liquid foliar to PH17AW maize plants at 2, 4, and 6 weeks after transplant and 3.4× foliar application of Metalosate® Copper liquid foliar to PH17AW maize plants 6 weeks after transplant.

TABLE 5

Transformation Frequency with Copper Sprayed PH17AW maize plants, 3.4× at 6 Weeks vs. 3.4× at 2, 4, 6 Weeks

| | 3.4× @ 6 weeks | | 3.4× @ 2, 4, 6 weeks | |
|---|---|---|---|---|
| | copper spray | control | copper spray | control |
| Total # constructs | 6 | 6 | 5 | 5 |
| Total # ears | 25 | 25 | 13 | 16 |
| Total # embryos | 3728 | 3277 | 1746 | 2362 |
| Total # callus events | 951 | 932 | 394 | 382 |
| % ave tx freq | 25.5% | 28.4% | 22.6% | 16.2% |

Table 5 Statistical Analysis:
Differences in the transformation frequency between treatments were analyzed using Chi Square. In this experiment, application of 3.4× Metalosate® Copper liquid foliar to PH17AW maize occurring at 6 weeks after transplant yielded statistically significant reduction of transformation frequency when compared to the control ($p \leq 0.01$). Application of 3.4× Metalosate® Copper liquid foliar to PH17AW maize occurring at 2, 4, 6 weeks after transplant yielded significantly increased transformation frequency when compared to the control ($p \leq 0.001$).

Example 8

Determining Changes in Plant Tissue Targets for the Application of Metalosate® Copper Liquid Foliar In addition to foliar applications of Metalosate® Copper liquid foliar, transformation frequency may be improved by applying Metalosate® Copper liquid foliar to excised PH17AW immature maize embryos prior to transformation and plating where; maize embryos could be excised from the ear, treated with a Metalosate® Copper liquid foliar solution, for example using a soak or spray application, and the treated embryos could optionally be rinsed with sterile distilled water to remove exogenous Metalosate® Copper liquid solution. Excised PH17AW embryos could then be transformed using known transformation techniques as described above.

Example 9

Metalosate® Copper Liquid Foliar Increase Transformation Frequency of Biolistics Process Biolistic maize transformation may be practiced as detailed Ranch et al (U.S. Pat. No. 7,022,894, and U.S. Pat.

No. 7,057,089). Immature embryos are derived from selfed High Type II source plants or High Type II source plants fertilized with pollen from elite commercial genotypes. Prior to pollination, the embryo source plants are treated with Metalosate® Copper liquid foliar, or not, as described in Examples 1-3. by applying the foliar solution in the range of about 3.4 times to about 13.6 times the recommended field rate. Ears from the plants are harvested 7-10 days after pollination, and aseptically prepared following standard methods for maize transformation of immature embryos. The immature embryos are plated onto high osmoticum medium with no plant growth regulators, and bombarded with PHP5128. (ubi:ubi1zmintron1:gus:pinii//camv35senh:camv35s:omega:adh1intron1:bar:pinii) associated with gold microprojectile particles. BAR is the selectable marker gene, and transgenic events are selected under herbicide selection. After bombardment, the immature embryos are transferred to medium containing the selective agent, bialaphos. After about 6-8 weeks, transgenic events can be picked from the various treatments and scored as described in Example 5. That population of embryos which are derived from plants treated with Metalosate® Copper liquid foliar are expected to have a significantly higher transformation frequency—that is, a greater yield of transgenic events per unit of fresh immature embryos bombarded as compared to embryos from control plants.

That which is claimed:

1. A method of transforming a maize plant cell comprising: applying to a maize plant as a foliar spray an effective amount of copper amino acid chelate, wherein said copper amino acid chelate is applied at about 0.75% to about 9% of copper amino acid chelate per acre, and wherein the application occurs at three or more different ages of the maize plant;
preparing an explant from said maize plant following the application of the copper amino acid chelate; and
transforming the explant with a polynucleotide of interest, wherein the transformation frequency of the explant from the maize plant treated with the effective amount of the copper amino acid chelate is increased compared to a transformation frequency of an explant from a maize plant not treated with the copper amino acid chelate.

2. The method of claim 1, wherein the copper amino acid chelate is selected from the group consisting of 4% w/w Copper amino acid chelate foliar liquid and 16% w/w Copper amino acid chelate foliar powder.

3. The method of claim 1, wherein the copper amino acid chelate comprises copper that is bound to a first amino acid and a second amino acid, wherein the first and second amino acids are chelated with the copper or wherein the first amino acid is chelated with the copper and the second amino acid is not chelated with the copper.

4. The method of claim 3, wherein the first and second amino acids of the copper amino acid chelate are different.

5. The method of claim 1, wherein said effective amount of copper amino acid chelate comprises about 4% w/w copper amino acid chelate per gallon applied at a rate of at least about 20 ounces per acre.

6. The method of claim 1, comprising applying to the plant copper amino acid chelate comprising about 4% w/w copper amino acid chelate per gallon at a rate of from about 20 ounces per acre to about 140 ounces per acre.

7. The method of claim 2, comprising applying to the plant the foliar liquid comprising copper amino acid chelate in an amount of about 0.75% per acre to about 3.5% per acre.

8. The method of claim 1, comprising applying the copper amino acid chelate to the plant, wherein the plant is in stage selected from the group consisting of a vegetative stage of growth or a reproductive stage of growth.

9. The method of claim 8, wherein the vegetative stage is selected from the group consisting of V-1, V-2, V-3, V-4, V-5, V-6, V-7, V-8, V-9, V-10, V-11, V-12, V-13, V-14, V-15, V-16, V-17, V-18 and VT.

10. The method of claim 8, wherein the reproductive stage of growth is R1.

11. The method of claim 1, wherein preparing the explant comprises excising a plant cell or tissue from the explant.

12. The method of claim 1, wherein the explant from the plant comprises an embryo, a callus, a cotyledon, a hypocotyl, an epicotyl, a meristem, a seedling, a seed, a leaf, a stem, a shoot, a scutellum, a node, a leaf base, a root, an ear, or a tassel.

13. The method of claim 12, wherein the embryo comprises an immature zygotic embryo.

14. The method of claim 1, further comprising transforming the explant using *Agrobacterium*, electroporation, microinjection, or biolistic bombardment.

15. The method of claim 1, wherein the explant is stably transformed.

16. The method of claim 1, further comprising regenerating a plant from the transformed explant.

* * * * *

UNITED STATES PATENT AND TRADEMARK OFFICE
CERTIFICATE OF CORRECTION

| | | |
|---|---|---|
| PATENT NO. | : 8,367,913 B2 | Page 1 of 1 |
| APPLICATION NO. | : 12/846320 | |
| DATED | : February 5, 2013 | |
| INVENTOR(S) | : Tiwari et al. | |

It is certified that error appears in the above-identified patent and that said Letters Patent is hereby corrected as shown below:

IN THE SPECIFICATION

Column 4, line 56, delete "leaf" and insert --leaf.-- therefor.

Column 12, line 43, delete "1s" and insert --Is-- therefor.

Signed and Sealed this
Thirtieth Day of July, 2013

Teresa Stanek Rea
*Acting Director of the United States Patent and Trademark Office*